United States Patent [19]

Gupta

[11] 4,146,034

[45] Mar. 27, 1979

[54] ENDOTRACHEAL TUBE CONNECTOR

[75] Inventor: Badri N. Gupta, Los Angeles, Calif.

[73] Assignee: Shiley Scientific, Inc., Irvine, Calif.

[21] Appl. No.: 802,699

[22] Filed: Jun. 2, 1977

[51] Int. Cl.² .............................................. A61M 16/00
[52] U.S. Cl. ..................................... 128/351; 285/176; 285/332
[58] Field of Search ............................... 128/348–351; 285/176, 260, 332, 332.4

[56] References Cited

U.S. PATENT DOCUMENTS

| | | | |
|---|---|---|---|
| 2,638,096 | 5/1953 | Waldhaus | 128/348 |
| 3,399,668 | 9/1968 | Lundgren | 128/348 X |
| 3,880,168 | 4/1975 | Berman | 128/351 |
| 3,973,569 | 8/1976 | Sheridan et al. | 128/351 |

Primary Examiner—Dalton L. Truluck

[57] ABSTRACT

A connector for connecting an endotracheal tube and the like to a source of air or gas. In the preferred embodiment, the end of the connector which fits into the tube is constructed with a bevel cut from the top of the connector to a point between the center line of the connector and the bottom thereof. As described below, this configuration substantially facilitates the insertion of the connector into the tube and avoids damaging the tube during the assembly procedure. Alternative embodiments of the tube end of the connector are also disclosed.

7 Claims, 6 Drawing Figures

U.S. Patent  Mar. 27, 1979  4,146,034
FIG. 1.
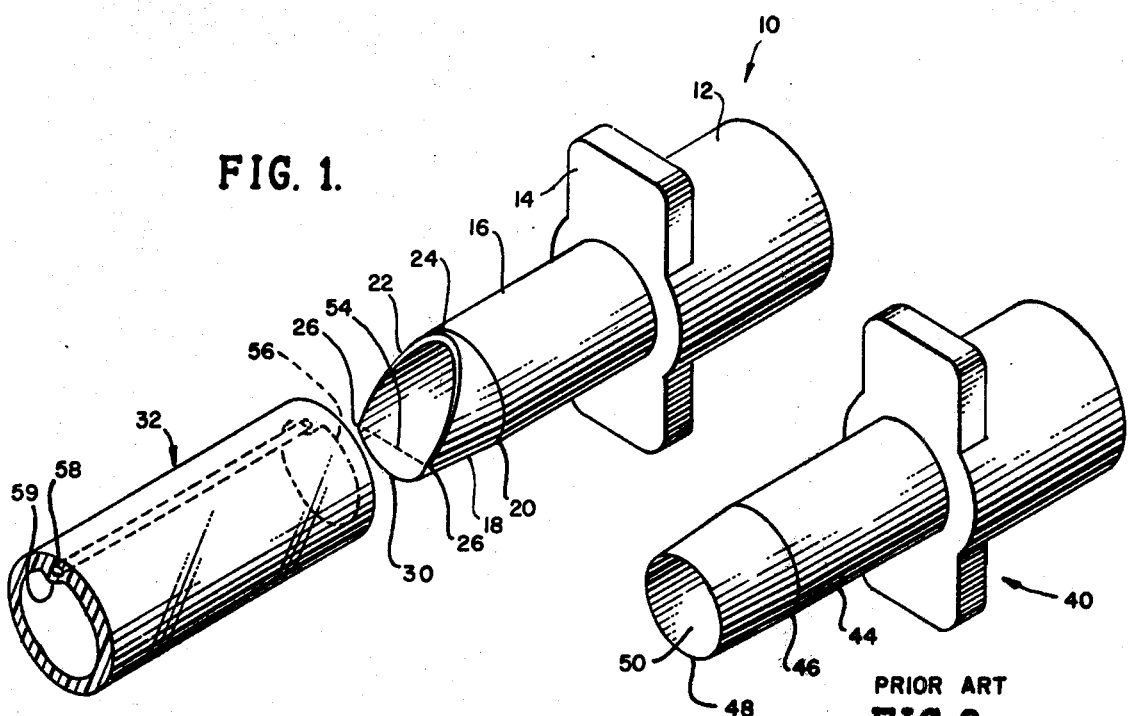
PRIOR ART
FIG. 2.
FIG. 3.
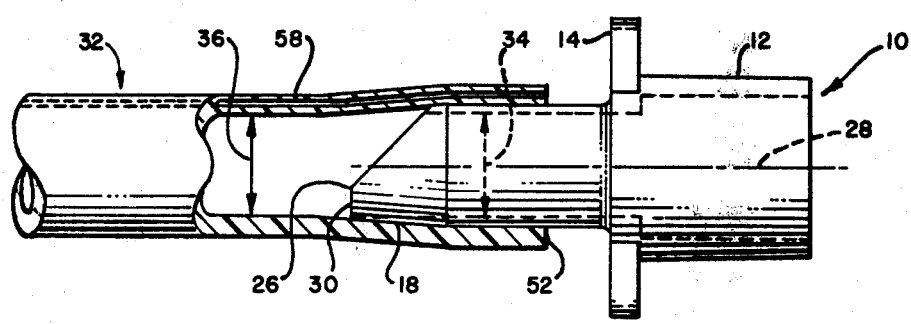
FIG. 4.  FIG. 5.  FIG. 6.
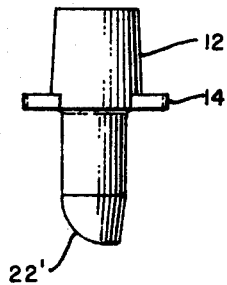 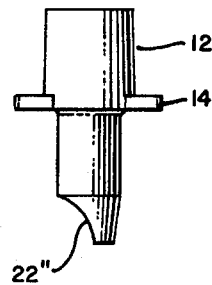 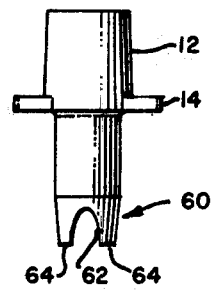

ENDOTRACHEAL TUBE CONNECTOR

BACKGROUND OF THE INVENTION

The present invention relates to devices which are used to connect an endotracheal tube to the source of air or other gas, such as anesthetic gas, which the medical practitioner desires to introduce into a patient's respiratory system. Specifically, this invention pertains to an improved construction of the patient end of the connector, i.e. the end which fits into the gas-source end of the endotracheal tube.

The endotracheal tube connectors currently in use all share a common configuration for the patient end. This configuration consists basically of a cylindrical barrel whose inside diameter is the same as the inside diameter of the tube in order to ensure an airtight fit, maximum gas flow, and minimum turbulence. Typically, the outside diameter of the outer cylindrical barrel is tapered at the patient end to facilitate insertion into the tube.

Several problems with this configuration have arisen in practice. The requirement that the inside diameter of the connector be equal to that of the tube results in the outside diameter of the connector being greater than the inside diameter of the tube. This results in considerable difficulty in inserting the connector into the tube, even when the barrel diameter is reduced on a taper. This difficulty is increased in practice because the physician normally cuts the endotracheal tube to the desired length during the medical procedure, and the cutting operation often squeezes the tube, resulting in a tube end with an oval cross-sectional shape. Also, the walls of endotracheal tubes very often contain a cuff inflation lumen. This structure also results in a non-circular tube cross section which contributes to the difficulty of inserting the prior art connectors. Ease of assembly is critical in the medical application of the endotracheal tube, as the time spent inserting the connector may mean the difference between the life and the death of the patient.

Also, the standard connector, as previously described, requires significant care for proper insertion. This is due to the fact that the reduced barrel diameter at the patient end results in a very thin wall section which is prone to damage in the process of insertion. Such damage may result in an obstruction which diminishes gas flow and/or increases turbulence and may make catheter insertion more difficult, or require the use of an undersize catheter. Minute pieces of the edge of the connector may also be broken off, resulting in the inhalation of foreign particles by the patient. The care required for insertion also adds measurably to the time required for assembling the endotracheal apparatus.

SUMMARY OF THE INVENTION

The present invention overcomes the above-mentioned problems by the use of a modified shape for the patient end of the connector. This shape maintains the required equality of the respective inside diameters of the connector and the tube, while facilitating quick and easy insertion into endotracheal tubes of non-circular cross section. The necessary airflow characteristics are maintained, as is the necessary structural strength of the connector, and the probability of damage to the patient end of the connector is minimized.

Several configurations for the patient end of the endotracheal tube connector may be used in carrying out the present invention in accordance with the above objectives. In the preferred embodiment, the tapered barrel forming the patient end of the connector is constructed with a straight angular bevel. This bevel starts at the top of the barrel a small distance outward of the start of the taper, then extends downward and outward at an angle of approximately 45 degrees to a point between the longitudinal axis of the connector and the bottom of the barrel. This beveled cut produces a blunt, squared-off leading edge at the patient end of the connector. The maximum width across this leading edge is less than the inside diameter of the connector and, therefore, less than the inside diameter of the tube. The leading edge can, therefore, serve as a guide for quick alignment of the connector with the endotracheal tube, so that the connector may be accurately inserted into the tube with relative ease and with a minimum probability of damaging the end of the connector by the striking thereof against the wall of the tube. The squared-off leading edge is preferred, since it maintains the structural strength of the connector, thereby also serving to minimize damage. However, the straight bevel may extend all the way to the bottom periphery of the connector if desired.

Alternative embodiments which also carry out the intended objectives of the invention include the substitution of a convex or a concave arcuate bevels for the straight angular bevel. Another alternative embodiment consists of two or more arcuate slots cut into the tapered portion of the connector, these slots formed along diametrically opposite sides of the periphery thereof when only two slots are used.

DESCRIPTION OF DRAWINGS

The characteristics and advantages of the invention are best understood by reference to the drawings.

FIG. 1 is a perspective view of the preferred embodiment of the endotracheal tube connector showing the position of the connector with respect to the end of a typical endotracheal tube prior to the insertion of the connector into the tube.

FIG. 2 is a perspective view of the typical prior art connector.

FIG. 3 is a side elevation of the preferred embodiment of the invention inserted into the endotracheal tube.

FIGS. 4, 5 and 6 are side elevation views of alternative embodiments of the present invention.

DESCRIPTION OF THE INVENTION

Referring to the drawings, FIGS. 1 and 3 depict the preferred embodiment of the connector which is the subject of the present application. The connector 10 is comprised of a cylindrical inlet barrel 12, a grasping flange 14, and a cylindrical outlet barrel 16. The outside diameter of the outlet barrel (which forms the patient end of the connector) is reduced in a tapered outlet end portion 18 which begins at a circumferential line 20 around the outlet barrel. This tapered portion 18 is cut to form a straight beveled edge 22 which has a corner 24 located on one periphery of the tapered portion 18 a short distance from the circumferential line 20. From the corner 24, the bevel 22 extends downward and outward at an angle of approximately 45 degrees to corners 26, which are located between the longitudinal axis 28 of the connector and the periphery of the tapered portion 18 diametrically opposite the corner 24. The result is a blunt, squared-off arcuate leading edge 30 which is defined by the corners 26 and the periphery of the tapered portion 18 which is diametrically opposite the corner 24.

As shown in FIGS. 1 and 3, the leading edge 30 formed by the bevel 22 serves as a guide and a wedge to facilitate easy insertion of the connector into the endotracheal tube 32. In FIG. 3 it can be seen that the inside diameter 34 of the connector is equal to the inside diameter 36 of the tube. This equality of the respective inside diameters ensures an airtight fit, maximum gas flow, and minimum turbulence. The bevel 22, since it does not extend beyond line 20, does not interfere with proper gripping of cylindrical barrel 16 by tube 32. Thus, the gripping force between these parts 10 and 32 is not compromised.

The significant differences and advantages of a connector with a guiding leading edge, such as that designated by the numeral 30, are easily demonstrated by a comparison with the typical prior art connector 40, such as is currently in widespread use, which is illustrated in FIG. 2. The prior art connector 40 includes a cylindrical barrel 44 whose outer diameter begins to taper at circumferential line 46, and terminates at a thin circular leading edge 48 which defines the circular outlet opening 50. With this construction, it is easy to see that during the process of inserting the connector into the endotracheal tube, any part of the thin leading edge 48 may be struck against the wall 52 of the endotracheal tube 32 unless substantial care is taken during the insertion process. The damage which is the likely result of such striking may be in the form of a deformation of the leading edge 48, which would cause an obstruction in the gas flow, or it may result in minute pieces breaking off of the leading edge 48, thereby resulting in the inhalation of foreign particles by the patient.

These disadvantages are overcome in the present invention by the use of the beveled outlet end of the connector. The bevel results in the leading edge 30, which acts both as a guide for quick and easy alignment of the connector with the tube, and as a wedge to facilitate the insertion of the connector into the tube. This guiding and wedging action is accomplished by the extension of the bevel 22 to below the longitudinal axis 28 of the connector. The result is that the maximum width 54 of the leading edge 30 is less than the inside diameter 34 of the connector, and, therefore, it is less than the inside diameter 36 of the tube, since the respective inside diameters of the connector and the tube are equal. This allows the leading edge 30 to be located in the tube inlet opening 56 at the start of the insertion process, with substantial clearance between the edge 30 and the tube wall 52. The connector can then be pushed into the tube, with the bevel 22 serving to guide the connector into place, while the taper 18 gradually wedges the connector into the required tight fit in the tube. As a result of the concerted guiding and wedging actions of the bevel 22 and the taper 18, little effort is required to align the connector with the tube opening 56, while allowing the insertion of the connector into the tube with little or no likelihood of having the leading edge 30 strike the end of the tube wall 52. The leading edge 30 is also substantially smaller, in terms of arc length, than the leading edge 48 of the prior art connector. These characteristics serve to minimize not only the care (and therefore the time) required for the proper insertion of the connector, but also the probability of damage to the leading edge of the connector during the insertion process.

The above-mentioned advantages of the present invention are even more marked where the endotracheal tube has a non-circular cross section. This is the usual situation due to two factors. First, the typical endotracheal tube 2, as depicted in FIGS. 1 and 3, contains a cuff inflation lumen 58 within the wall of the tube. This presents an intrusion into the otherwise circular inlet opening 56 in the form of the ridge 59 which acts as an obstruction against which the leading edge 48 of the prior art connector is prone to strike, and which therefore increases the difficulty of inserting the prior art connector. Also, in practice, the inlet end of the tube 32 is often cut by the medical practitioner. This results in an oval cross-sectional shape for the inlet opening 56 which also serves to increase the difficulty of inserting the circular edge 48 of the prior art connector. The present invention minimizes the problem of the non-circular tube end cross section through the increased guiding and wedging action of the leading edge 30, as compared to that of the leading edge 48 of the prior art connector. Also, the substantially smaller size of the leading edge 30, as compared to the leading edge 48, results in a significantly diminished likelihood that the lumen ridge 59 will obstruct insertion.

FIG. 4 illustrates an alternative embodiment of the present invention, wherein a convexly arcuate bevel 22' is used instead of the straight bevel 22 of the preferred embodiment.

FIG. 5 presents another alternative embodiment which uses a concavely arcuate bevel 22".

The embodiments depicted in FIGS. 4 and 5 generally offer the same advantages as does the preferred embodiment, but they do not afford quite the same ease of construction.

FIG. 6 illustrates still another embodiment of the invention which incorporates a tapered end portion 60 similar to that of the prior art but with two arcuate slots 62 cut into the tapered portion along diametrically opposite sides of the periphery thereof. The shape of these slots may be altered or their number increased without departing from the concept. For example, the slots may be triangular or rectangular in shape. This configuration offers similar advantages to those of the preferred embodiment, and the use of this configuration, where two slots are used as shown in FIG. 6, requires the squeezing together of the tabs 64 formed by the slots 62 in order to facilitate insertion.

What is claimed is:

1. A connector for connecting an endotracheal tube or the like to a source of gas, comprising:
   a gas inlet means;
   a grasping means extending from the periphery of said inlet means;
   a cylindrical outlet means sharing a common longitudinal axis with said inlet means and extending downstream therefrom;
   a patient end portion sharing a common longitudinal axis with said cylindrical outlet means and extending downstream therefrom, said patient end portion having a tapered outside diameter; and
   means for providing a blunt, squared-off, arcuate leading edge at the extreme downstream end of said patient end portion, the maximum width of said leading edge being defined by a line across said extreme downstream end between said longitudinal axis of said patient end portion and the periphery thereof, said line having a length less than the inside diameter of said cylindrical outlet means so that said leading edge is quickly and easily inserted into an endotracheal tube having an inside diameter substantially equal to the inside diameter of said cylindrical outlet means, and so that the likelihood of said leading edge being struck and damaged by the end of the endotracheal tube during insertion is substantially reduced.

2. A connector for connecting an endotracheal tube or the like to a source of gas, as defined in claim 1, wherein said means for providing said leading edge comprises a beveled portion starting at the top of said patient end portion a short distance downstream of the juncture of said patient end portion and said cylindrical outlet means, thence extending downstream and downward and terminating at said line defining said maximum width.

3. A connector for connecting an endotracheal tube or the like to a source of gas, as defined in claim 2, wherein said beveled portion is linear and angled with respect to said patient end portion.

4. A connector for connecting an endotracheal tube or the like to a source of gas, as defined in claim 2, wherein said beveled portion comprises a convex arcuate configuration.

5. A connector for connecting an endotracheal tube or the like to a source of gas, as defined in claim 2, wherein said beveled portion comprises a concave arcuate configuration.

6. A connector for connecting an endotracheal tube or the like to a source of gas, as defined in claim 1, wherein said means for providing said leading edge comprises a pair of longitudinal slots along diametrically opposite sides of the periphery of said patient end portion.

7. A connector for connecting an endotracheal tube or the like to a source of gas, comprising:
   a cylindrical inlet barrel;
   a grasping flange extending from the periphery of said inlet barrel;
   a cylindrical outlet barrel, having an inside diameter substantially equal to the inside diameter of said endotracheal tube, said outlet barrel sharing a common longitudinal axis with said cylindrical inlet barrel and extending downstream therefrom;
   a patient end portion sharing a common longitudinal axis with said cylindrical outlet barrel and extending downstream therefrom, said patient end portion having a tapered outside diameter and an inside diameter which is substantially equal to the inside diameter of said endotracheal tube; and
   means for providing a blunt, squared-off, arcuate leading edge at the extreme downstream end of said patient end portion, the maximum width of said leading edge being defined by a line across said extreme downstream end between said longitudinal axis of said patient end portion and the bottom periphery thereof, said line having a length less than the inside diameter of cylindrical outlet barrel for facilitating the insertion of said outlet barrel into said endotracheal tube, said means comprising a beveled portion starting at the top of said patient end portion a short distance downstream of the juncture of the patient end portion and the cylindrical outlet barrel, and terminating at said line defining said maximum width.

* * * * *